United States Patent
Aoki et al.

(10) Patent No.: US 6,255,428 B1
(45) Date of Patent: Jul. 3, 2001

(54) PREPARATION OF EPOXY GROUP-BEARING ORGANOPOLYSILOXANE OR ORGANOSILANE

(75) Inventors: Shunji Aoki; Toshio Ohba, both of Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 09/409,988

(22) Filed: Sep. 30, 1999

(30) Foreign Application Priority Data

Sep. 30, 1998 (JP) .................................................. 10-293101

(51) Int. Cl.⁷ ............................ C08G 77/08; C08G 77/06
(52) U.S. Cl. ................................ 528/15; 528/32; 528/31; 549/215; 502/158; 558/303
(58) Field of Search .................... 528/15, 32, 31; 549/215; 502/158; 558/303

(56) References Cited

U.S. PATENT DOCUMENTS 5,128,431  *  7/1992  Riding et al. .
5,258,480     11/1993  Eckberg et al. .
5,260,399     11/1993  Crivello et al. .
5,391,676  *   2/1995  Eckberg et al. .

FOREIGN PATENT DOCUMENTS 0415243A   3/1991  (EP) .
0652247A   5/1995  (EP) .
6-32906    2/1994  (JP) .
6136126    5/1994  (JP) .

* cited by examiner

*Primary Examiner*—Robert Dawson
*Assistant Examiner*—Kuo-Liang Peng
(74) *Attorney, Agent, or Firm*—Birch, Stewart, Kolasch & Birch, LLP

(57) ABSTRACT

An epoxy group-bearing organopolysiloxane or organosilane is prepared by effecting addition reaction between an organohydropolysiloxane or organohydrosilane and an alkenyl group-bearing epoxy compound in the presence of an addition reaction catalyst. A cyano group-bearing compound is co-present in the reaction system. The end organopolysiloxane or organosilane having a stabilized viscosity is obtained while avoiding gelation or thickening during reaction.

8 Claims, No Drawings

PREPARATION OF EPOXY GROUP-BEARING ORGANOPOLYSILOXANE OR ORGANOSILANE

This invention relates to a process for preparing an epoxy group-bearing organopolysiloxane or organosilane.

BACKGROUND OF THE INVENTION

An epoxy group-bearing organopolysiloxane or organosilane is prepared by effecting addition reaction between SiH groups on an organohydropolysiloxane or organohydrosilane and alkenyl groups on an alkenyl group-bearing epoxy compound in the presence of a catalyst.

During this addition reaction, polymerization reaction of epoxy groups can take place as a side reaction, resulting in a reaction product having a substantially increased viscosity or being gelled. The thickening and gelation become outstanding particularly when the alkenyl group-bearing epoxy compound is added dropwise to a mixture of the organohydropolysiloxane and the addition reaction catalyst, or when the addition reaction catalyst is added to a mixture of the organohydropolysiloxane and the alkenyl group-bearing epoxy compound to conduct batch reaction.

One known process of preparing an epoxy group-bearing organopolysiloxane while suppressing polymerization of epoxy groups involves mixing a SiH group-bearing silane or siloxane with a tertiary amine and a hydrosilylation catalyst, and reacting the mixture with an olefin epoxide to produce an epoxy silicone (see JP-A 6-32906). While the epoxy silicone is often used in such an application as a coating to be cured with an acid generator, typically an onium salt, this process has a possibility that the tertiary amine be left in the epoxy silicone and restrain the silicone from being cured with the acid generator.

It is also known from JP-A 6-136126 to prepare an epoxy silicone by effecting addition reaction between an organohydrogensiloxane or organohydrogensilane and an ethylenically unsaturated epoxide in the presence of a hydrosilylation catalyst comprising a phosphine ligand and a phosphine-free transition metal complex. Depending on the amount of the phosphine ligand relative to the phosphine-free transition metal complex, there can arise a problem that gelation occurs due to the polymerization of epoxy groups or the addition reaction does not proceed at all.

Therefore, an object of the invention is to provide a novel and improved process for preparing an epoxy group-bearing organopolysiloxane or organosilane through addition reaction between an organohydropolysiloxane or organohydrosilane and an alkenyl group-bearing epoxy compound while avoiding the undesired phenomenon of gelation or thickening.

SUMMARY OF THE INVENTION

The invention is directed to a process for preparing an epoxy group-bearing organopolysiloxane or organosilane by effecting addition reaction between an organohydropolysiloxane or organohydrosilane and an alkenyl group-bearing epoxy compound in the presence of an addition reaction catalyst. The inventor has found that when a cyano group-bearing compound is added to the reaction system, quite unexpectedly, neither gelation nor thickening occurs during the reaction. The viscosity of the epoxy group-bearing organopolysiloxane or organosilane being produced is stabilized.

The invention provides a process for preparing an epoxy group-bearing organopolysiloxane or organosilane by effecting addition reaction between SiH groups on an organohydropolysiloxane or organohydrosilane and alkenyl groups on an alkenyl group-bearing epoxy compound in the presence of an addition reaction catalyst, characterized in that a cyano group-bearing compound is co-present during the reaction.

DESCRIPTION OF THE PREFERRED EMBODIMENTS

The process of the invention starts with an organohydropolysiloxane or organohydrosilane, which is not critical insofar as it has at least one SiH group in a molecule. Straight, branched or cyclic ones may be used. Typical organohydropolysiloxanes are given below although the invention is not limited thereto.

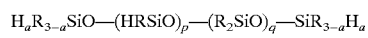

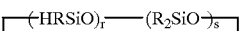

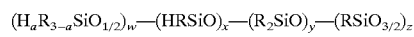

Herein, R represents substituted or unsubstituted monovalent hydrocarbon groups of 1 to 10 carbon atoms, for example, alkyl groups such as methyl, ethyl, propyl and butyl, cycloalkyl groups such as cyclohexyl, aryl groups such as phenyl and tolyl, and substituted ones of these groups in which some or all of the hydrogen atoms attached to carbon atoms are replaced by hydroxyl groups, cyano groups or halogen atoms, such as hydroxypropyl, cyanoethyl, 3-chloropropyl, and 3,3,3-trifluoropropyl.

Letter a is an integer of 0 to 3, p and q are integers inclusive of 0, and the sum of p+q is such a number that the organohydropolysiloxane may have a viscosity of about 0.5 to 50,000 centipoise at 25° C., with the proviso that a and p are not equal to 0 at the same time. Letter r is an integer of at least 1, s is an integer inclusive of 0, and the sum of r+s is at least 3, preferably from 3 to 20. Letters w and z are integers of at least 1, x and y are integers inclusive of 0, and the sum of w+x+y+z is such a number that the organohydropolysiloxane may have a viscosity of about 1 to 50,000 centipoise at 25° C., with the proviso that a and x are not equal to 0 at the same time.

Preferably the organohydropolysiloxane has a viscosity of about 10 to 10,000 centipoise at 25° C. A mixture of two or more organohydropolysiloxanes is also useful.

Several illustrative examples of the organohydropolysiloxane are given below. In the following formulae and throughout the specification, Me is methyl.

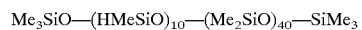

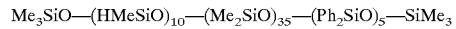

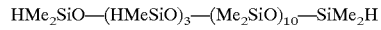

 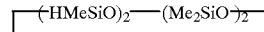

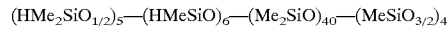

Typical organohydrosilanes are represented by the following formula although the invention is not limited thereto.

$$H_bSiR'_{4-b}$$

Herein, b is an integer of 1 to 4, and R' represents substituted or unsubstituted monovalent hydrocarbon groups of 1 to 10 carbon atoms, alkoxy groups of 1 to 10 carbon atoms, halogen atoms or similar groups. Exemplary groups represented by R' are alkyl groups such as methyl, ethyl, propyl and butyl, cycloalkyl groups such as cyclohexyl, aryl groups such as phenyl and tolyl, substituted ones of these groups in which some or all of the hydrogen atoms attached to carbon atoms are replaced by hydroxyl groups, cyano groups or halogen atoms, such as hydroxypropyl, cyanoethyl, 3-chloropropyl, and 3,3,3-trifluoropropyl as well as methoxy, ethoxy, and phenoxy groups and chlorine atoms.

Another starting reactant is an alkenyl group-bearing epoxy compound which is an organic compound having at least one epoxy group and at least one alkenyl group in a molecule. Examples include 4-vinylcyclohexene oxide, 4-isopropenyl-1-methylcyclohexene oxide, allyl glycidyl ether, 1,5-hexadiene monoxide, and glycidyl (meth)acrylate, with the 4-vinylcyclohexene oxide and allyl glycidyl ether being preferred.

For reaction, the organohydropolysiloxane or organohydrosilane and the alkenyl group-bearing epoxy compound are preferably used in such a proportion that the number of alkenyl groups is greater than the number of SiH groups, that is, the molar ratio of alkenyl groups to SiH groups is at least 1.00, more preferably from 1.05 to 1.5.

Platinum catalysts and rhodium catalysts are exemplary of the addition reaction catalyst, with the platinum catalysts being preferred. Examples include chloroplatinic acid, alcohol solutions of chloroplatinic acid, reaction products of chloroplatinic acid with alcohols, reaction products of chloroplatinic acid with olefins, and reaction products of chloroplatinic acid with vinyl group-bearing siloxanes.

The amount of the addition reaction catalyst used is not critical. Preferably the catalyst is used in such an amount as to provide about 1 to 10,000 ppm, and more preferably about 1 to 500 ppm of a platinum group metal (e.g., platinum or rhodium element) based on the alkenyl group-bearing epoxy compound.

According to the invention, a cyano group-bearing compound is added to the reaction system. It is an organic compound having at least one cyano group in a molecule and typically represented by the following general formula.

$$R''{-}CN$$

Herein, R" represents substituted or unsubstituted monovalent hydrocarbon groups of 1 to 20 carbon atoms, for example, alkyl groups such as methyl, ethyl, propyl and butyl, cycloalkyl groups such as cyclohexyl, alkenyl groups such as vinyl and allyl, aryl groups such as phenyl and tolyl, and substituted ones of these groups in which some or all of the hydrogen atoms attached to carbon atoms are replaced by hydroxyl groups, cyano groups or halogen atoms, such as hydroxypropyl, cyanoethyl, 3-chloropropyl, and 3,3,3-trifluoropropyl.

At the end of reaction, the cyano group-bearing compound is removed from the reaction mixture. Such removal is done simply by co-distillation with the solvent under heat and vacuum. From this standpoint, cyano group-bearing compounds having a boiling point of up to 300° C. under atmospheric pressure are preferable.

Preferred examples of the cyano group-bearing compound include acetonitrile, propionitrile, butyronitrile, isobutyronitrile, valeronitrile, acrylonitrile, succinonitrile, benzonitrile, and α-tolunitrile. Of these, acetonitrile and benzonitrile are especially preferred on account of easy distillation at the end of reaction.

An appropriate amount of the cyano group-bearing compound is about 10 ppm or more, more preferably about 100 ppm or more based on the alkenyl group-bearing epoxy compound. The upper limit is usually 10% by weight based on the alkenyl group-bearing epoxy compound though not critical.

The process for preparing an epoxy group-bearing organopolysiloxane or organosilane according to the invention may be carried out in the following different ways although the invention is not limited thereto. In a first embodiment, the alkenyl group-bearing epoxy compound is added dropwise to a mixture of the organohydropolysiloxane or organohydrosilane, the addition reaction catalyst, and the cyano group-bearing compound. In a second embodiment, the organohydropolysiloxane or organohydrosilane is added dropwise to a mixture of the alkenyl group-bearing epoxy compound, the addition reaction catalyst, and the cyano group-bearing compound. In a third embodiment, the addition reaction catalyst is added dropwise to a mixture of the organohydropolysiloxane or organohydrosilane, the alkenyl group-bearing epoxy compound, and the cyano group-bearing compound.

Addition reaction is usually carried out at room temperature to about 300° C. The reaction proceeds fast when heated above 40° C. The reaction time is not critical. The reaction is carried out in a solvent if necessary. The solvents used herein include aromatic hydrocarbon solvents such as toluene and xylene, aliphatic hydrocarbon solvents such as hexane and octane, ketone solvents such as methyl ethyl ketone and methyl isobutyl ketone, ester solvents such as ethyl acetate and isobutyl acetate, ether solvents such as diisopropyl ether and 1,4-dioxane, alcohol solvents such as isopropanol, and mixtures thereof. Of these, the aromatic and aliphatic hydrocarbon solvents are preferable. It is also possible to use the cyano group-bearing compound as a reaction solvent. The reaction atmosphere may be air or an inert gas.

At the end of addition reaction, the addition reaction catalyst is removed from the reaction mixture as by water washing or activated carbon treatment, if necessary. When the solvent is used, it is distilled off under heat and/or vacuum. By working up in this way, the epoxy group-bearing organopolysiloxane or organosilane is collected.

The epoxy group-bearing organopolysiloxanes obtained by the inventive process are exemplified by the following formulae.

$$E_aR_{3-a}SiO{-}(ERSiO)_p{-}(R_2SiO)_q{-}SiR_{3-a}E_a$$

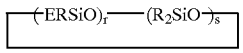

$$(E_aR_{3-a}SiO_{1/2})_w{-}(ERSiO)_x{-}(R_2SiO)_y{-}(RSiO_{3/2})_z{-}E_bSiR'_{4-b}$$

Herein, R, R', a, b, r, s, w, x, y, and z are as defined above, and E is an epoxy group-containing organic group.

Specific examples are given below.

$$Me_3SiO{-}(EMeSiO)_{10}{-}(Me_2SiO)_{40}{-}SiMe_3$$

$$Me_3SiO{-}(EMeSiO)_6{-}SiMe_3$$

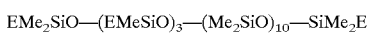

  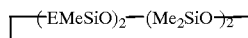

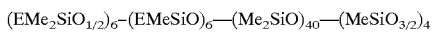

E is an epoxy group-containing organic group, examples of which are given below.

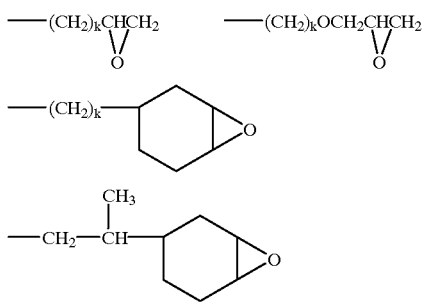

Herein, k is a number of 1 to 10, especially 2 to 8.

EXAMPLE

Examples of the invention are given below by way of illustration and not by way of limitation. All parts are by weight.

Example 1

A four-necked flask equipped with a stirrer, thermometer, reflux condenser and dropping funnel was charged with 9.22 parts of toluene, 6.01 parts of 1,3,5,7-tetramethylcyclotetrasiloxane, 14.9 parts of 4-vinylcyclohexene oxide, and 0.53 part of benzonitrile and held at 70° C. To the flask was added 0.20 part of a 0.5% toluene solution of a platinum catalyst. Vigorous exothermic reaction took place, but no gel formed. The reaction mixture was cooled to 70° C. and stirred for one hour. The toluene and volatiles were distilled off at 80° C. and 3 Torr, yielding 18.0 parts of a brown clear liquid. On analysis by GPC, IR, and $^1$H-NMR, this was identified to be an epoxy group-bearing organopolysiloxane of the following formula (I).

(I)

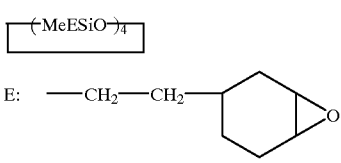

Example 2

Reaction was carried out as in Example 1 except that 0.21 part of acetonitrile was used in lieu of 0.53 part of benzonitrile. Similarly vigorous exothermic reaction took place, but no gel formed. The epoxy group-bearing organopolysiloxane of formula (I) was obtained.

Example 3

A four-necked flask equipped with a stirrer, thermometer, reflux condenser and dropping funnel was charged with 9.22 parts of toluene, 6.01 parts of 1,3,5,7-tetramethylcyclotetrasiloxane, and 0.53 part of benzonitrile. 0.20 part of a 0.5% toluene solution of a platinum catalyst was added to the flask, which was held at 70° C. Then 14.9 parts of 4-vinylcyclohexene oxide was added dropwise over 2 hours. The reaction mixture was further stirred for one hour. The toluene and volatiles were distilled off at 80° C. and 3 Torr, yielding 17.9 parts of a brown clear liquid. On analysis by GPC, IR, and $^1$H-NMR, this was identified to be the epoxy group-bearing organopolysiloxane of formula (I).

Example 4

A four-necked flask equipped with a stirrer, thermometer, reflux condenser and dropping funnel was charged with 6.01 parts of 1,3,5,7-tetramethylcyclotetrasiloxane and 9.22 parts of benzonitrile. 0.20 part of a 0.5% toluene solution of a platinum catalyst was added to the flask, which was held at 70° C. Then 14.9 parts of 4-vinylcyclohexene oxide was added dropwise over 2 hours. The reaction mixture was further stirred for one hour. The olatiles were distilled off at 80° C. and 3 Torr, yielding 18.1 parts of a brown clear liquid of formula (I).

Example 5

A four-necked flask equipped with a stirrer, thermometer, reflux condenser and dropping funnel was charged with 172 parts of toluene, 4.12 parts of benzonitrile, and 437 parts of an organohydropolysiloxane having the following average compositional formula.

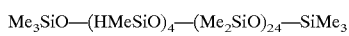

0.94 part of a 0.5% toluene solution of a platinum catalyst was added to the flask, which was held at 70° C. To the flask, 119 parts of 4-vinylcyclohexene oxide was added dropwise over 2 hours. After the completion of dropwise addition, the reaction mixture was stirred for one hour at 70° C. The toluene and volatiles were distilled off at 80° C. and 3 Torr, yielding 520 parts of a brown clear liquid having a viscosity of 102 centipoise. On analysis by GPC, IR, and $^1$H-NMR, this was identified to be an epoxy group-bearing organopolysiloxane of the following formula (II).

(II)

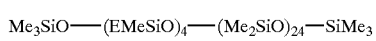

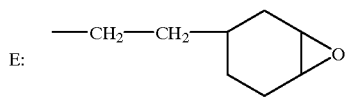

Example 6

A four-necked flask equipped with a stirrer, thermometer, reflux condenser and dropping funnel was charged with 74.5 parts of toluene, 0.52 part of benzonitrile, and 56.1 parts of trimethoxysilane. 0.20 part of a 0.5% toluene solution of a platinum catalyst was added to the flask, which was held at 70° C. To the flask, 74.5 parts of 4-vinylcyclohexene oxide was added dropwise over 2 hours. After the completion of dropwise addition, the reaction mixture was stirred for one hour at 70° C. Distillation of the reaction mixture yielded 91 parts of a pale yellow clear liquid. On analysis by GPC, IR, and $^1$H-NMR, this was identified to be an epoxy group-bearing organosilane of the following formula.

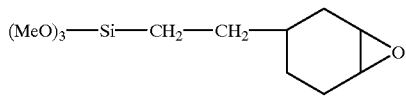

Comparative Example 1

A four-necked flask equipped with a stirrer, thermometer, reflux condenser and dropping funnel was charged with 9.22 parts of toluene, 6.01 parts of 1,3,5,7-tetramethylcyclotetrasiloxane, and 14.9 parts of 4-vinylcyclohexene oxide and held at 70° C. To the flask was added 0.20 part of a 0.5% toluene solution of a platinum catalyst whereupon vigorous exothermic reaction took place, and a gel formed immediately.

Comparative Example 2

A four-necked flask equipped with a stirrer, thermometer, ref lux condenser and dropping funnel was charged with 9.22 parts of toluene and 6.01 parts of 1,3,5,7-tetramethylcyclotetrasiloxane. 0.20 part of a 0.5% toluene solution of a platinum catalyst was added to the flask, which was held at 70° C. To the flask, 14.9 parts of 4-vinylcyclohexene oxide was added dropwise. A gel formed when an about 1/10 portion was added.

According to the invention, an epoxy group-bearing organopolysiloxane or organosilane having a stabilized viscosity is obtained while avoiding gelation or thickening during reaction.

Japanese Patent Application No. 10-293101 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing an epoxy group-bearing organopolysiloxane or organosilane, comprising the step of effecting addition reaction between SiH groups on an organohydropolysiloxane or organohydrosilane and alkenyl groups on an alkenyl group-bearing epoxy compound in the presence of an addition reaction catalyst and a cyano group-bearing compound.

2. The process of claim 1 wherein the step of effecting addition reaction includes charging a reactor with a mixture of the organohydropolysiloxane or organohydrosilane and the cyano group-bearing compound and adding dropwise the alkenyl group-bearing epoxy compound to the mixture.

3. The process of claim 1 wherein the addition reaction catalyst is a platinum catalyst.

4. The process of claim 1 wherein the cyano group-bearing compound is benzonitrile or acetonitrile.

5. The process of claim 1 wherein the alkenyl group-bearing epoxy compound is a member selected from the group consisting of 4-vinylcyclohexene oxide, 4-isopropenyl-1-methylcyclohexene oxide, allyl glycidyl ether, 1,5-hexadiene monoxide, and glycidyl (meth)acrylate.

6. The process of claim 1 wherein the molar ratio of alkenyl groups to SiH groups is from 1.05 to 1.5.

7. The process of claim 1 wherein the addition reaction is carried out in a solvent.

8. The process of claim 7, comprising the further step of removing the cyano group-bearing compound by co-distillation with the solvent under heat and vacuum at the end of the addition reaction.

* * * * *